US009474547B2

(12) United States Patent
Katra et al.

(10) Patent No.: US 9,474,547 B2
(45) Date of Patent: Oct. 25, 2016

(54) TUNNELING TOOL FOR DELIBERATE PLACEMENT OF AN ILR

(71) Applicant: Greatbatch Ltd., Clarence, NY (US)

(72) Inventors: Rodolphe Katra, Blaine, MN (US); Walter J. Dobrovolny, St Paul, MN (US); Scott Kimmel, St Paul, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/886,444

(22) Filed: Oct. 19, 2015

(65) Prior Publication Data

US 2016/0038181 A1    Feb. 11, 2016

Related U.S. Application Data

(63) Continuation of application No. 13/889,779, filed on May 8, 2013, now Pat. No. 9,161,775.

(60) Provisional application No. 61/644,184, filed on May 8, 2012.

(51) Int. Cl.
*A61B 17/32* (2006.01)
*A61B 17/34* (2006.01)
(Continued)

(52) U.S. Cl.
CPC ......... *A61B 17/3468* (2013.01); *A61B 5/0402* (2013.01); *A61B 5/042* (2013.01); *A61B 5/6847* (2013.01); *A61B 17/3209* (2013.01); *A61M 25/0668* (2013.01); *A61B 5/0006* (2013.01);
(Continued)

(58) Field of Classification Search
CPC .............. A61B 17/3468; A61B 5/042; A61B 2560/063; A61B 17/3209; A61B 17/3415; A61F 2002/9511; A61M 2005/14252; A61M 2005/14284; A61M 2005/1585; A61M 25/0194; A61M 25/0612
USPC ........ 606/170, 167, 108, 129, 185; 600/423, 600/424, 365; 607/115–116, 4, 9; 623/1.11, 623/1.12
See application file for complete search history.

(56) References Cited

U.S. PATENT DOCUMENTS 3,943,936 A    3/1976 Rasor et al.
4,453,537 A    6/1984 Spitzer
(Continued)

FOREIGN PATENT DOCUMENTS

WO    8002231       10/1980
WO    2004041124    5/2004

OTHER PUBLICATIONS

Intsearch, PCT2009032640, dated Apr. 15, 2009.

*Primary Examiner* — Melanie Tyson
*Assistant Examiner* — Majid Jamialahmadi
(74) *Attorney, Agent, or Firm* — Michael F. Scalise

(57) ABSTRACT

A tunneling tool for implanting a medical device into body tissue is described. The tunneling tool comprises a first leg and a second leg. An intermediate portion of the second leg is shaped to nest a medical device therein. A hub connects the first and second distal leg ends together. A sheath providing a lumen extends from the hub to an open end distal of the first and second legs. The first and second legs are manipulatable to separate the hub and the sheath into two portions, a first split portion connected to the first leg and a second split portion connected to the second leg. When a medical device is nested in the tunneling tool, breaking the tunneling tool apart enables the first and second split portions to be removed from body tissue, leaving the implanted medical device behind.

20 Claims, 15 Drawing Sheets

US 9,474,547 B2

Page 2

(51) Int. Cl.
  *A61B 17/3209* (2006.01)
  *A61M 25/06* (2006.01)
  *A61B 5/042* (2006.01)
  *A61B 5/0402* (2006.01)
  *A61B 5/00* (2006.01)
  *A61B 5/0205* (2006.01)
  *A61B 5/053* (2006.01)

(52) U.S. Cl.
  CPC .............. *A61B 5/0205* (2013.01); *A61B 5/053* (2013.01); *A61B 5/686* (2013.01); *A61B 2017/320056* (2013.01); *A61B 2560/063* (2013.01)

(56) References Cited

U.S. PATENT DOCUMENTS

| | | | |
|---|---|---|---|
| 4,687,469 A | 8/1987 | Osypka | |
| 4,716,903 A | 1/1988 | Hansen et al. | |
| 4,974,600 A | 12/1990 | Reyes | |
| 5,113,869 A | 5/1992 | Nappholz et al. | |
| 5,269,326 A | 12/1993 | Verrier | |
| 5,313,953 A | 5/1994 | Yomtov et al. | |
| 5,324,312 A | 6/1994 | Stokes et al. | |
| 5,645,586 A | 7/1997 | Meltzer | |
| 5,741,211 A | 4/1998 | Renirie et al. | |
| 5,833,603 A | 11/1998 | Kovacs et al. | |
| 5,987,352 A | 11/1999 | Klein et al. | |
| 6,027,480 A | 2/2000 | Davis et al. | |
| 6,285,897 B1 | 9/2001 | Kilcoyne et al. | |
| 6,347,245 B1 | 2/2002 | Lee et al. | |
| 6,436,068 B1 | 8/2002 | Bardy | |
| 6,445,952 B1 | 9/2002 | Manrodt et al. | |
| 6,480,733 B1 | 11/2002 | Turcott | |
| 6,496,715 B1 | 12/2002 | Lee et al. | |
| 6,699,200 B2 | 3/2004 | Cao et al. | |
| 6,950,705 B2 | 9/2005 | Bardy et al. | |
| 7,107,093 B2 | 9/2006 | Burnes | |
| 7,107,103 B2 | 9/2006 | Schulman et al. | |
| 7,212,849 B2 | 5/2007 | Zhang et al. | |
| 7,299,086 B2 | 11/2007 | McCabe et al. | |
| 8,180,438 B2 | 5/2012 | Brockway et al. | |
| 8,280,499 B2 | 10/2012 | Brockway et al. | |
| 2001/0047314 A1 | 11/2001 | Linberg | |
| 2002/0035381 A1 | 3/2002 | Bardy et al. | |
| 2002/0040231 A1 | 4/2002 | Wysoki | |
| 2003/0004564 A1 | 1/2003 | Elkins et al. | |
| 2003/0050684 A1* | 3/2003 | Abrams | A61F 2/95 623/1.11 |
| 2003/0191504 A1 | 10/2003 | Meadows et al. | |
| 2005/0090779 A1 | 4/2005 | Osypka | |
| 2006/0004433 A1* | 1/2006 | Greenberg | A61F 2/07 623/1.11 |
| 2006/0217779 A1 | 9/2006 | Ransbury et al. | |
| 2007/0016089 A1 | 1/2007 | Fischell et al. | |
| 2008/0249379 A1 | 10/2008 | Furman | |
| 2009/0076522 A1 | 3/2009 | Shan | |
| 2009/0192381 A1 | 7/2009 | Brockway et al. | |
| 2009/0198153 A1* | 8/2009 | Shriver | A61B 17/00234 600/585 |
| 2010/0241069 A1* | 9/2010 | Hatten | A61F 2/958 604/96.01 |

* cited by examiner

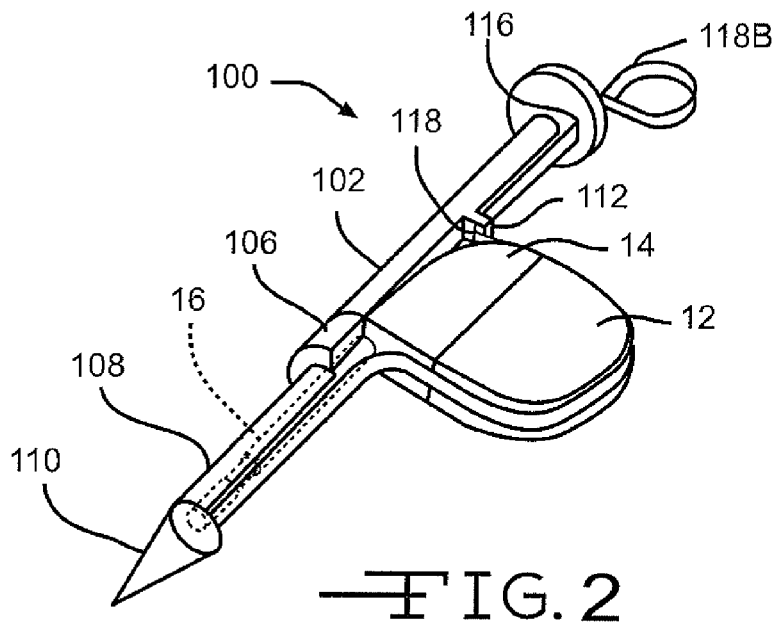
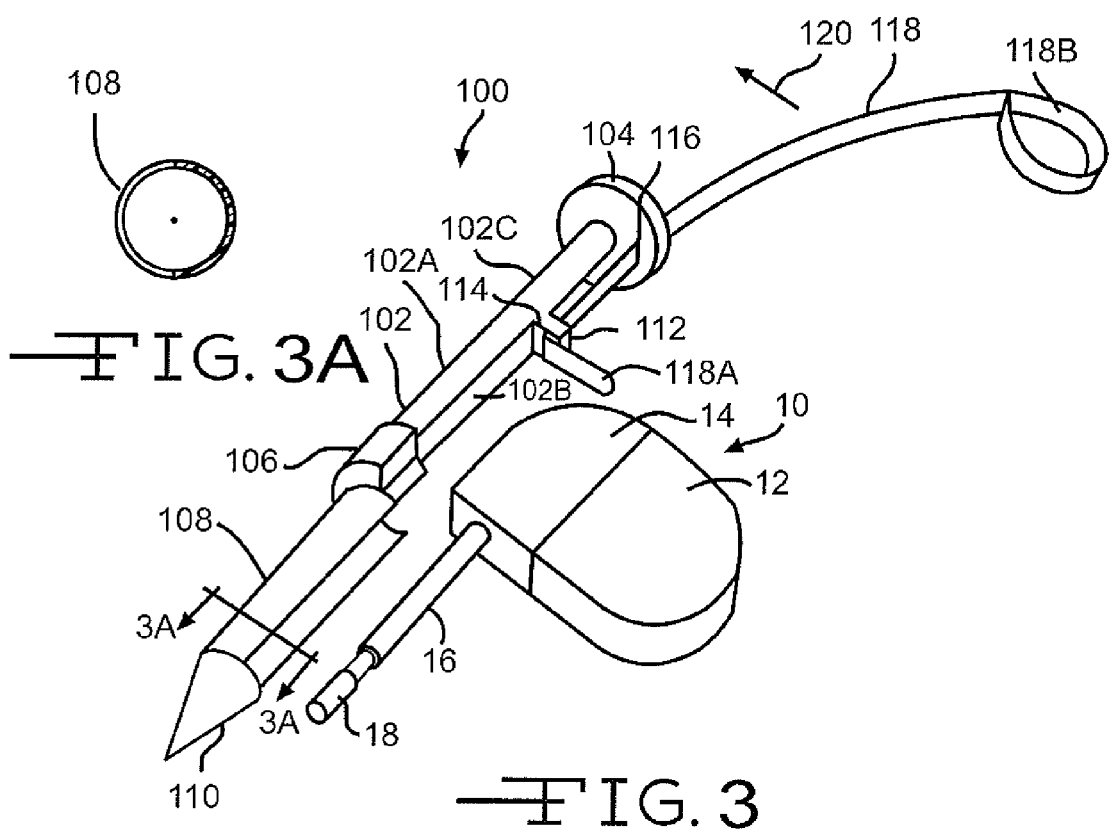

TUNNELING TOOL FOR DELIBERATE PLACEMENT OF AN ILR

CROSS REFERENCE TO RELATED APPLICATION

This application is a continuation of application Ser. No. 13/889,779, filed on May 8, 2013, now U.S. Pat. No. 9,161,775, which claims priority to U.S. provisional application Ser. No. 61/644,184, filed on May 8, 2012.

BACKGROUND OF THE INVENTION

1. Field of the Invention

This disclosure relates to implantable monitoring devices, and implantation systems and methods for implanting the monitoring devices at a subcutaneous implant location.

2. Prior Art

Implantable devices that monitor cardiac physiologic activity are frequently implanted subcutaneously under a patient's skin in the chest. An implantable loop recorder (ILR) is an example of a device that may be implanted in this fashion. The exemplary ILR 10 shown in FIG. 1 is shaped like a small pacemaker. The ILR comprises a housing 12 for the device electronics and battery power source. A header 14 is supported on the housing and contains conductors connected to the device electronics through one or more hermetic feedthroughs. An antenna 16 extends outwardly from a header 14. This device can be used to record an electrocardiogram (EGG) signal for the patient.

To implant the ILR device, a 25 mm incision is made, a subcutaneous pocket is formed near the incision, and a tunnel is formed to extend away from the pocket for placement of the flexible lead using a tool or finger. The ILR device may be inserted through the incision and placed in the subcutaneous pocket, tested for proper operation, and repositioned if necessary. The incision is then closed.

Implanting ILR devices in this manner may be difficult, especially for physicians who are not skilled in device implantation. If the ILR device is improperly implanted, undesirable complications for the patient or suboptimal device performance may result. In addition, tearing of tissue during formation of the pocket and tunnel, for example, may result in tissue bleeding that requires appropriate steps during surgery to avoid hematoma. In addition, it may be necessary to employ fluoroscopy to assure that the antenna is properly positioned under the skin. If not properly positioned, the ILR and antenna may require repositioning to obtain an optimal EGG signal. This may extend the surgery duration, which may increase risk of infection and trauma, as well as expense.

Accordingly a need exists for an improved insertion system for a simpler approach to insertion, shorter insertion time, reduced risk of complications, reduced expense, and a reduced need for expensive equipment, such as fluoroscopy, during device placement.

SUMMARY OF THE INVENTION

In a first general aspect, an implantable monitoring device such as, but not limited to, an implantable loop recorder (ILR) includes an antenna includes at least one sensing element. The device also includes a rigid main housing supporting a header connected to the antenna. The ILR device further includes a measurement circuit, which is housed within the housing and electrically coupled to the at least one sensing element of the antenna and at least another sensing element on an outside surface of the rigid main body. The measurement circuit is configured to measure a potential difference between the at least one sensing element of the antenna and the at least another sensing element of the housing.

A method of implanting an implantable monitoring device in a subcutaneous implant region of a patient includes introducing an insert device to the subcutaneous region of the patient. The insert device has an internal chamber that is generally in the shape of at least a portion of the implantable monitoring device. The method also includes inserting, after the insert device has been introduced to the subcutaneous region, the implantable monitoring device to the internal chamber of the insert device. The method further includes removing the insert device from the subcutaneous region while leaving the implantable monitoring device at the subcutaneous region.

In various implementations, removing the insert device from the subcutaneous region includes withdrawing, in a direction opposite that which it was introduced, the insert device from the subcutaneous region while applying pressure to the monitoring device, where the insert device includes a surface modification to reduce a tensile strength of the insert device. The subcutaneous region may be above a pectoral fascia of the patient. At least a portion of the subcutaneous region may be below a pectoral fascia of the patient, or the entire subcutaneous region may be below the pectoral fascia.

The details of one or more implementations are set forth in the accompanying drawings and the description below. Other features, objects, and advantages will be apparent from the description and drawings, and from the claims.

BRIEF DESCRIPTION OF THE DRAWINGS

FIG. 2 is a perspective view of a first embodiment of a tunneling tool 100 for implanting the implantable device 10.

FIG. 3 is a perspective view showing the tunneling tool 100 in FIG. 2 separated from the implantable device 10.

FIG. 3A is a cross-sectional view along lines 3A-3A of FIG. 3.

FIG. 10 is a perspective view showing a tunneling tool 300 according to the present invention comprising matable clamshells 304 and 306 separated from each in order to receive the holder 302 and implantable device 10 there between.

FIG. 14 is an exploded view showing the clamshells 304 and 306 with the intermediate holder 302 and implantable device 10 there between.

Like reference symbols in the various drawings indicate like elements.

DETAILED DESCRIPTION OF THE PREFERRED EMBODIMENTS

Figure 1:
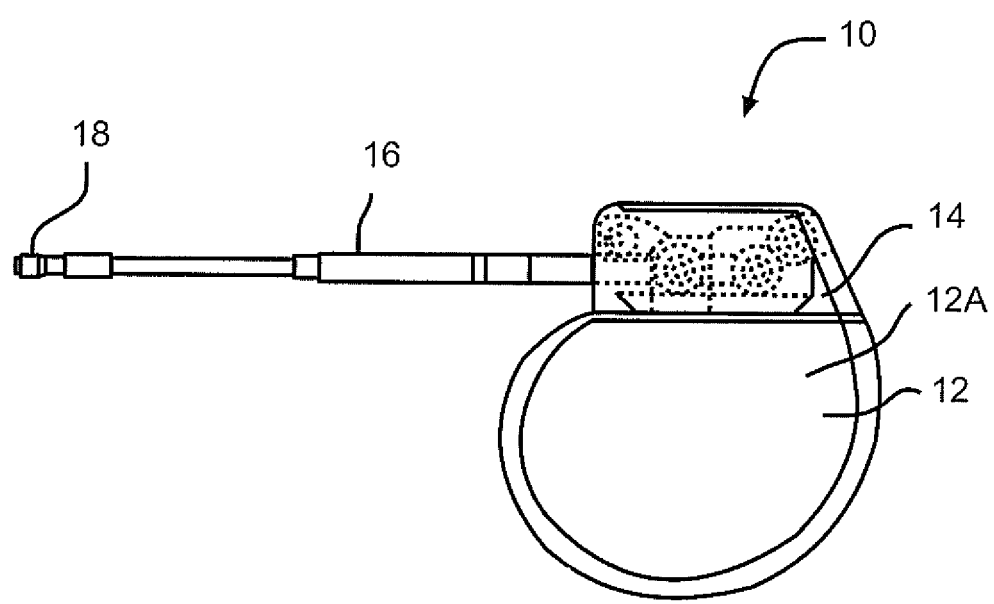
FIG. 1 is an elevation view of an exemplary implantable device 10 that can be subcutaneously implanted under a patient's skin.
Figure 4:
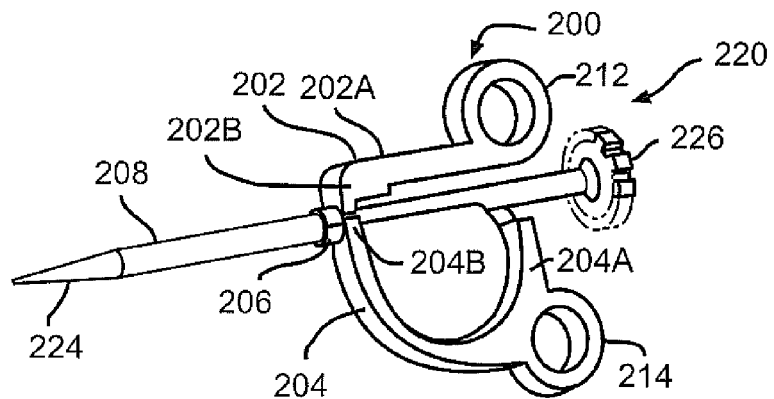
FIG. 4 is a perspective view of a second embodiment of a tunneling tool 200 according to the present invention coupled to a dilator 220.
Figure 5:
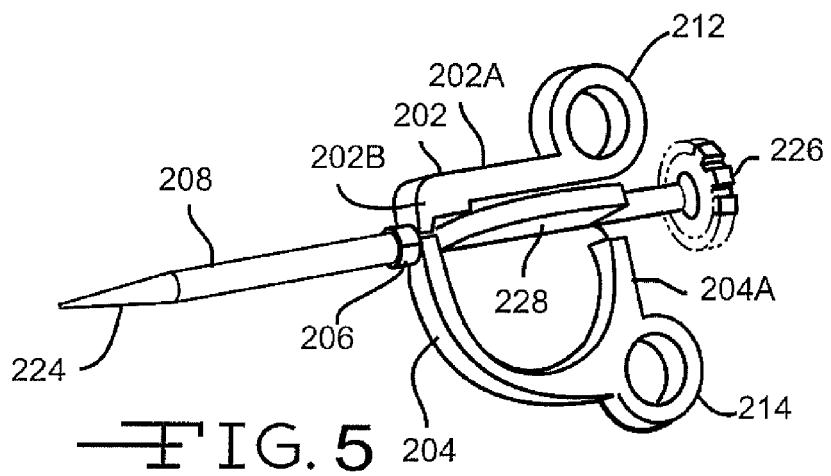
FIG. 5 is a perspective view showing the dilator 220 of FIG. 4 having been rotated 90° with respect to the tunneling tool 200.

Referring now to the drawings, FIG. 1 is an elevation view of an exemplary implantable device 10, such as an implantable loop recorder (ILR), which can be subcutaneously implanted under a patient's skin. The ILR comprises a housing 12 for the device electronics and battery power source. A header 14 is supported on the housing and contains conductors connected to the device electronics through one or more hermetic feedthroughs. An antenna 16 supporting a distal electrode 18 extends outwardly from the header 14. This device can be used to record an electrocardiogram (EGG) signal for the patient.

A first end of the flexible antenna 16 is attached at a fixation point to the header 14, and may generally flex or bend about the fixation point. The header 14 thus stabilizes the flexible antenna 16, yet allows it to bend and flex about the fixation point to conform to body tissue channel formation and subsequent tissue movement and flexing as the patient's muscles contract and expand during daily activities. In general, the flexible antenna 16 may bend at any appropriate angle with respect to the fixation point at the header 14, and in any appropriate direction.

The ILR device 10 may house a battery, which may be of a single-use or rechargeable chemistry, and circuitry (e.g., an electronics module) for performing actions consistent with the device's intended purpose. Without limitation, examples of actions that may be performed with some implementations of the device include measuring one or more physiologic signals, storing the measured signal(s) in memory within the device 10, processing collected data, wirelessly transmitting or receiving information to/from an external device, and others. In some embodiments, the housing 12 may contain a charging coil that can be excited (e.g., with an external charging coil placed in proximity to the implant location) to recharge a rechargeable battery of the device.

Using one of the tunneling tools and techniques discussed herein, the implantable ILR 10 may be implanted in a minimally invasive fashion that minimizes an incision size for insertion, minimizes trauma to body tissue during formation of an implant channel for the implantable device 10, minimizes risk of puncture or intrusion upon a muscle layer, intercostal space or body organ, and provides a fitted implant location closely tailored to actual device dimensions. Because incision size may be reduced as compared to previous implant techniques, a scar from the insertion may be less noticeable. Also, by forming an appropriately sized pocket for the implantable device 10, a risk of hematoma may be reduced. Further, the devices, systems and techniques disclosed herein may significantly reduce the time required for implantation, and may mitigate the need for fluoroscopy, thereby reducing the cost associated with the implantation procedure. Moreover, the simplicity of the approach described here may make implantation feasible in a procedure room or doctor's office, and may provide for consistently good results when implanted by physicians who lack experience and skills in placing implantable devices. For at least these reasons, physicians may prefer the systems, devices and techniques discussed herein when compared to presently available implant methods and devices.

By way of example, the device 10 may be a minimally invasive implantable monitoring device that senses and records a physiologic parameter, such as electrical activity of the heart, within a body of a patient. In some implementations, the device 10 is an implantable monitoring device that senses and records a physiologic parameter, such as an electrocardiogram (ECG) signal, within the body of the patient and wirelessly transmits information associated with the physiologic parameter to an external device. Such a monitoring-only device that records cardiac electrical information may be implanted in a human patient for a relatively short period of time, such as a few months for example. Other physiologic parameters or combinations of parameters, such as other electrical signals (e.g., EEG signal, EMG signal, neural signal, bio-impedance signal), mechanical signals (e.g., blood pressure signal, blood flow signal), chemical signals (e.g., glucose), temperature and the like may similarly be recorded by the device 10 in various implementations.

In some implementations, the device 10 may be relatively small, and may be sized and shaped for convenient implantation within a body of a patient, such as at a subcutaneous implant site, for example, in a pectoral region of a human patient, as will be discussed in more detail below. A tunneling tool according to the present invention may be used to directly insert the ILR 10 to a subcutaneous implant location.

The ILR device 10 may include one or more electrodes for electrically interfacing to surrounding tissue for the purpose of sensing electrical activity. In some implementations, the device 10 includes two electrodes. For example, FIG. 1 shows an implantable device with an exterior surface of the housing 12 providing a proximal electrode 12A. A distal electrode 18 is located at the end of the antenna 16. The implantable device is programmed to measure a potential difference (e.g., a subcutaneous ECG signal) between the proximal and distal electrodes 12A, 18. The electrodes 12A and 18 are each near a longitudinal end of the device 10. This placement may maximize signal vector length of a measured physiologic signal. In general, measured amplitude of a sensed physiologic signal, such as an ECG signal, will vary with device placement and orientation within the patient. Sensed signal amplitude may also be related to separation distance between the measuring electrodes. Positioning the electrodes 12A, 18 near opposite ends of the device 10 may maximize the amplitude of the sensed physiologic signal for a given device length, which may lead to better measurement results. In other implementations, device 10 includes three or more electrodes.

In some implementations, one of the electrodes may comprise an excitation electrode or combination excitation/sense electrodes. As an example, the device may measure a bio-impedance for diagnostic purposes by injecting a known current between the electrodes and measuring a resulting voltage there between two electrodes. The electrodes may comprise a conductive material such as titanium.

FIGS. 2, 3 and 3A illustrate a first embodiment of a tunneling tool 100 according to the present invention. The tunneling tool 100 comprises a shaft 102 extending to a proximal handle plate 104. The shaft 102 extends distally to a first, minor inverted U-shaped dilator channel 106 connected to a second, major inverted U-shaped dilator channel 108. The distal channel 108 terminates at a pointed piercing tip 110.

The shaft 102 has a radiused sidewall 102A meeting a planar bottom wall 102B extending along a portion of the shaft length. A proximal shaft portion 102C has a circular cross-section perpendicular to its length. A depending tab 112 delineates the planar bottom wall 102B from the proximal shaft portion 102C. The tab 112 has a first slot 114 of a generally rectangular cross-section. The long axis of the slot 114 is aligned generally parallel to the planar wall 102B of the shaft 102. A second slot 116 is provided in the handle plate 104, spaced laterally from the proximal shaft portion 102C and aligned axially with the first slot 114. In a similar manner, the second slot 116 has a generally rectangular cross-section with its long axis aligned parallel to the long axis of the first slot 114. The minor inverted channel 106 is sized to have a proximal portion of the antenna 16 where it connects to the header 14 of the ILR nested therein. The remainder of the antenna 16 nests in the major inverted channel 108.

In use, the ILR 10 is moved into close proximity to the tunneling tool 100 until the header 14 contacts the planar bottom wall 102B of the shaft 102 and the antenna 16 nests in the first and second inverted channels 106, 108. A flexible strap-type rip cord 118 has its distal end 118A releasably secured to the dilator tip 110. In that manner, the rip cord 118 covers the annular portion of the antenna 16 which is left exposed when the antenna is nested in the first and second channel portions 106, 108. The rip cord 118 extends over and around the header 14 beneath the antenna 16 and then along the curved side wall of the device housing 12 to the first tab slot 114 and finally the handle plate slot 118. A grasping portion 118B of the rip cord resides adjacent to the handle plate 104, opposite the ILR.

The tunneling tool 100 may comprise a semi-flexible, semi-rigid polyethylene material in various implementations. In some implementations, the distal dilator channel 108 is sufficiently flexible to deflect upon contacting a muscle layer during the introduction process. For example, as the tunneling tool 100 is inserted through an incision in the skin and through a fatty tissue layer below the skin, when the distal dilator 108 (see FIG. 24) contacts a muscle layer below the fatty tissue layer, which may generally be harder and more dense than the fatty tissue layer, the distal dilator may deflect so that the tunneling tool 100 slides across the top of the muscle layer rather than penetrating into the muscle layer. That is, as the tunneling tool 100 is urged through a fatty tissue layer of the body below the skin at an angle relative to the muscle layer, when the distal dilator 108 contacts the muscle layer, the dilator should deflect to slide across the muscle layer, substantially parallel to the muscle layer, even though the shaft 102 of the tunneling tool 100 may continue to be urged at the same angle relative to the muscle layer. This may increase patient safety, as muscle layer or intercostal space puncture may be avoided even if the physician directs the tunneling tool at a steeper-than-appropriate angle with respect to the muscle layer. The semi-flexible dilator 108 should nevertheless be rigid enough to provide direction and maintain its shape and orientation without substantial flexing as the tunneling tool 100 is introduced through the skin layer and the fatty tissue layer.

Figure 24:
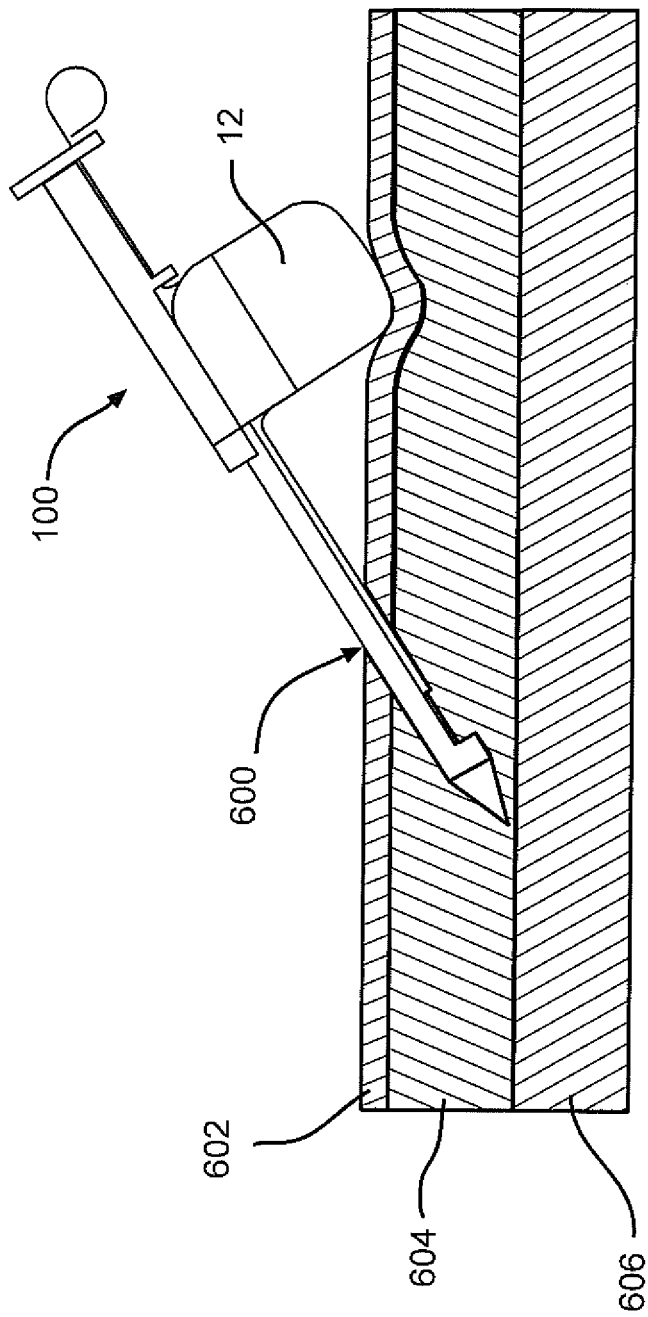
FIG. 24 is a side elevational view, partly in cross-section, of a tunneling tool 100 being moved into an incision 600 and a fatty tissue layer 604 to implant the implantable device 10 therein.

FIG. 24 is a view of tunneling tool 100 being introduced through an incision 600 in a skin layer 602 and through a fatty tissue layer 604. The distal tip 110 of the tunneling tool 100 is approaching a muscle layer 606 as the tool is urged through the incision 600, skin layer 602, and fatty tissue layer 604, as by a physician. The distal dilator 108 may deflect and slide along a top surface 608 of the muscle layer 606 without penetrating the muscle layer. When the tunneling tool 100 has been introduced to the desired implant site location, the surgeon pulls gently on the grasping portion 118B of the rip cord. This causes the rip cord 118 to release from the dilator tip 110 and slide along the lead 16, header 14 and device housing 12 until it reaches the depending tab 112. Once the rip cord 118 has released from the ILR 10, the tunneling tool 100 is moved in a lateral direction, as indicated by arrow 120, until it completely separates from the ILR. The tunneling tool 100 is now moved in a proximal direction, out of the incision, leaving the ILR behind.

Figure 25:
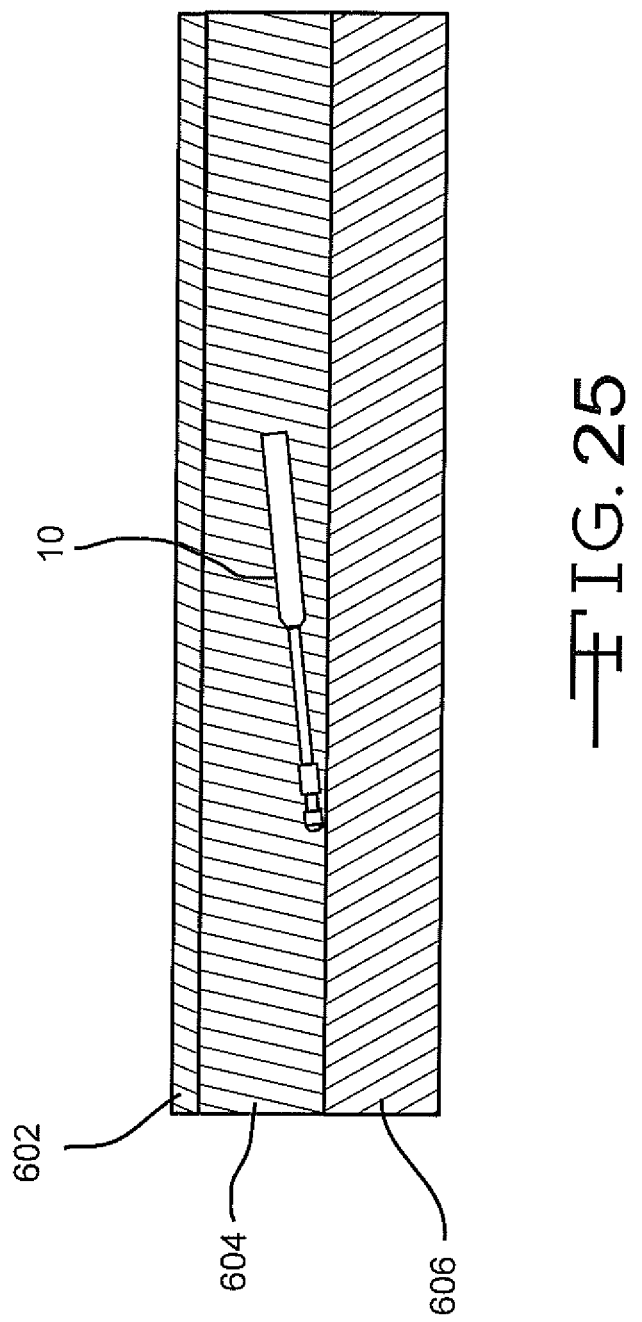
FIG. 25 is a side elevational view, partly in cross-section, of the implantable device 10 implanted in a fatty tissue layer 604.
Figure 26:
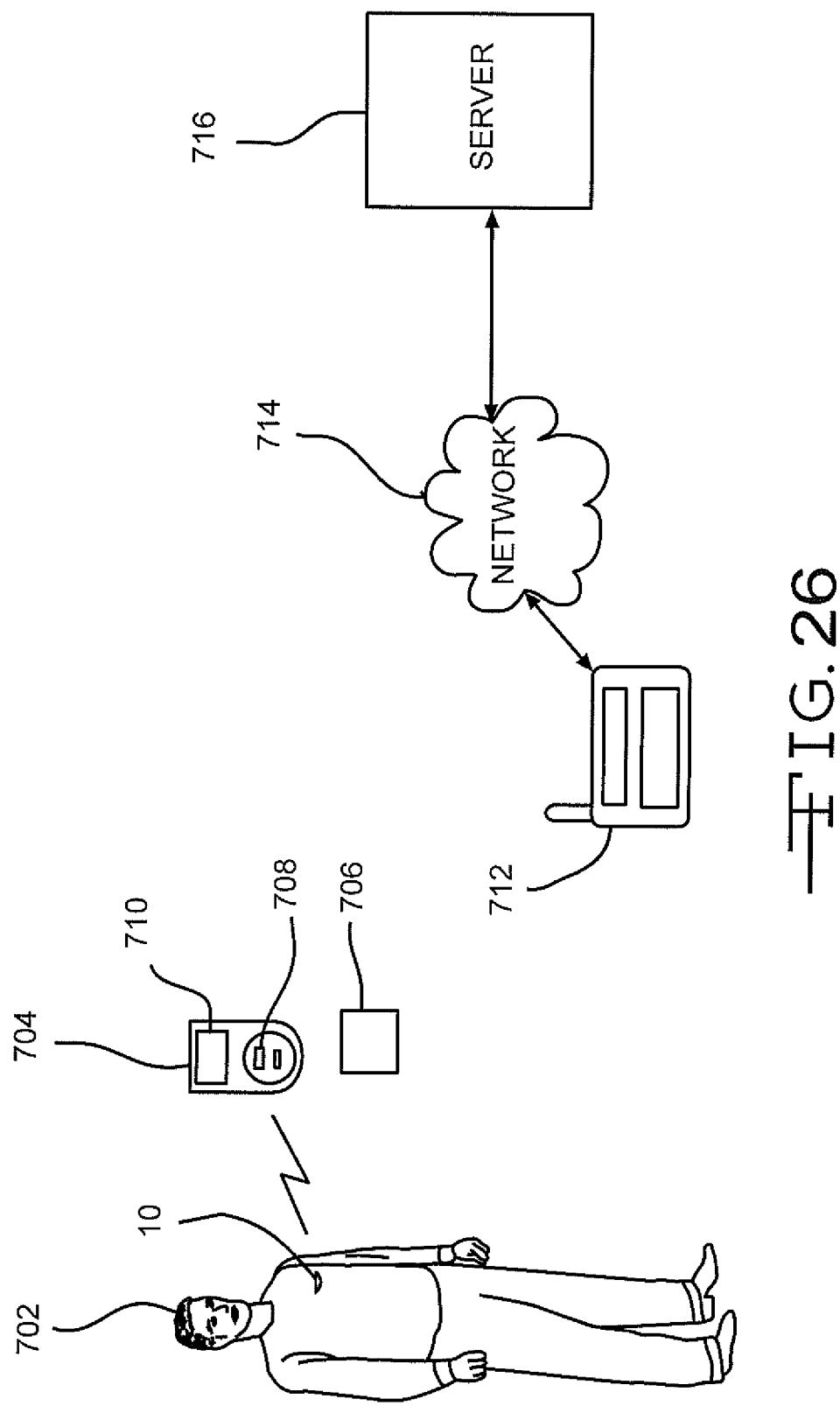
FIG. 26 is a diagram of an exemplary system 700 including the implantable device 10 implanted in a body of a patient 702 and ancillary equipment.

FIG. 25 is a view of the device 10 implanted subcutaneously in a patient using the tunneling tool 100. The ILR 10 is positioned at an implant site location below the skin 602 within the layer of fatty tissue 604, just above the muscle layer 606. The implant site location size and shape is closely matched to the size and shape of the ILR 10 because of the size and shape of the tunneling tool 100.

FIGS. 4 to 8 illustrate a second embodiment of a tunneling tool 200 according to the present invention. The tunneling tool 200 comprises spaced apart upper and lower or first and second handles 202 and 204 connected to a hub 206. The hub 206 is a sleeve-shaped member that supports a tubular sheath 208 opposite the handles 202, 204. The sheath 208 has a lumen (not shown) extending to an open distal end 210.

The upper handle 202 comprises an inverted L-shaped leg 202A having its distal end 202B connected to the hub 206. A finger ring 212 serving as a handgrip is at the proximal end of the long portion of the leg 202A. The lower handle 204 comprises a U-shaped handle portion 204A that is sized and shaped to receive the ILR nested therein. The distal end 204B of the lower handle is connected to the hub 206 opposite the upper handle 202. A proximal end 204C of the lower handle is adjacent to, but spaced from the upper handle. As will be explained in detail hereinafter, this distance is sufficient to receive the shaft of a dilator therein. A second finger ring 214 serving as a handgrip is connected to the U-shaped handle portion 204A, spaced from the proximal end 204C of the lower handle.

In that regard, the tunneling tool 200 is uniquely shaped to receive an implantable medical device nested in the U-shaped handle portion 204A. A first longitudinal axis A-A of the upper leg 202 is parallel to, but spaced from a second longitudinal axis B-B of the sheath lumen. This distance is depicted as "x" in FIG. 6. Further, a third longitudinal axis C-C of the proximal portion of the U-shaped handle 204 delineated between the handgrip 214 and the proximal handle end 204C is perpendicular to the first and second longitudinal axes. Moreover, a fourth longitudinal axis of a distal portion of the U-shaped handle 204 is parallel to the third longitudinal axis and perpendicular to the first and second axes.

A dilator 220 comprises a cylindrical shaft 222 with a pointed distal top 224. A hand wheel 226 is located at the proximal end of the shaft. A shaped body 228 is supported on the shaft 22 intermediate the tip 224 and hand wheel 226. The body 228 is sized and shaped to closely mimic the shape of the ILR 10.

Figure 6:
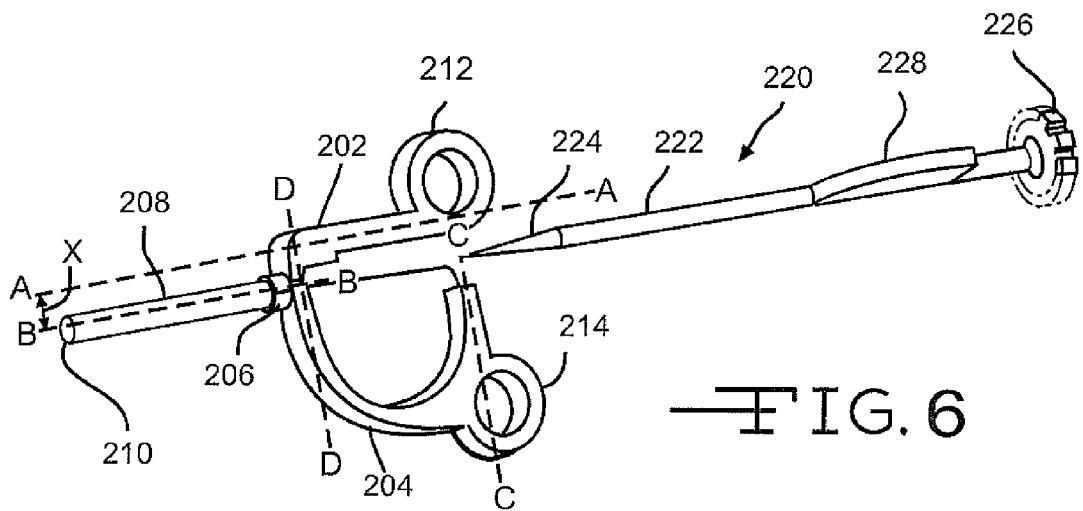
FIG. 6 is a perspective view showing the dilator 220 being removed from the tunneling tool 200 shown in FIG. 5.
Figure 7:
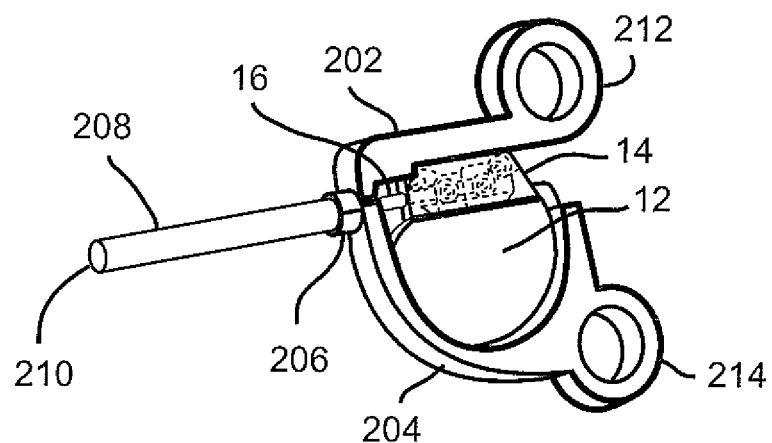
FIG. 7 is a perspective view showing the tunneling tool 200 carrying an implantable device 10.

In use, the dilator shaft 222 is moved into and through the sheath 208 until the tip 224 extends out through the open distal end 210 of the sheath. As this movement occurs, the shaped body 228 is rotated about perpendicular to the aligned planar surfaces of the upper and lower legs 202, 204. Once the shaped body 228 contacts the legs 202, 204 where they meet the hub 206, the hand wheel 226 is rotated to move the shaped body 228 into a nested alignment with the U-shaped portion 204B of the lower handle 204. This assembly is then moved into an incision until the shaped body 228 attached to the dilator 220 and carried by the tunneling tool 200 is below the fascia and in a position approximately where it is intended to be implanted. As shown in FIG. 6, the hand wheel 226 is manipulated to rotate the dilator 200 about 90° or until the shaped body 228 is clear of the lower leg 204. The dilator 220 is moved in a rearwardly direction as show in FIG. 7 to separate it from the tunneling tool 200. The tunneling tool 200 without the dilator is left in the incision with the U-shaped portion 204A of the lower leg 204 ready to receive the ILR.

Figure 8:
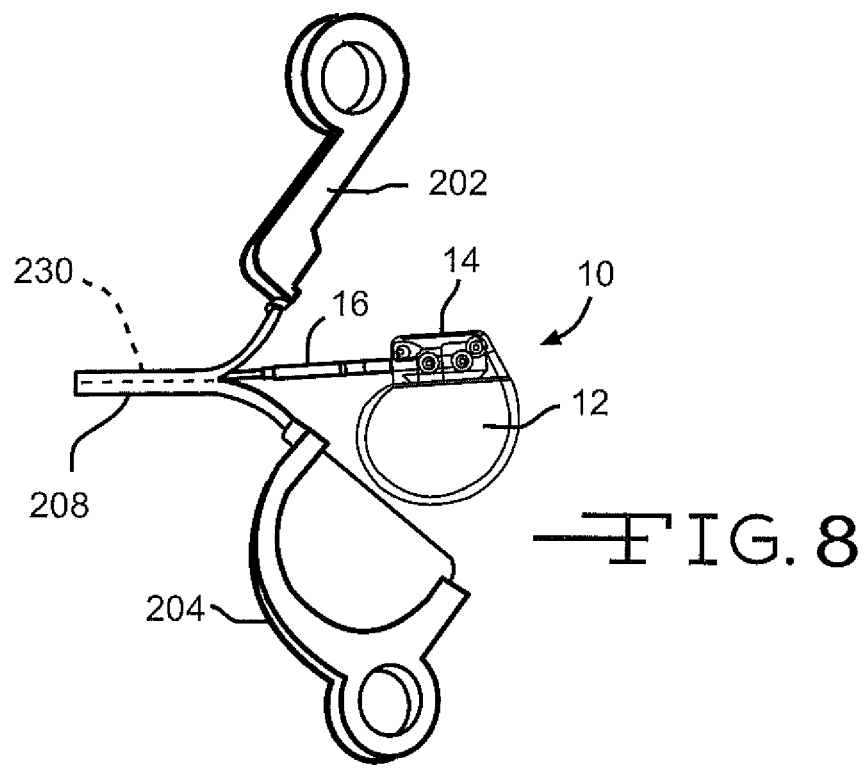
FIG. 8 is an elevation view of the tunneling tool of FIG. 7 being separated for release of the implantable device 10.
Figure 9:
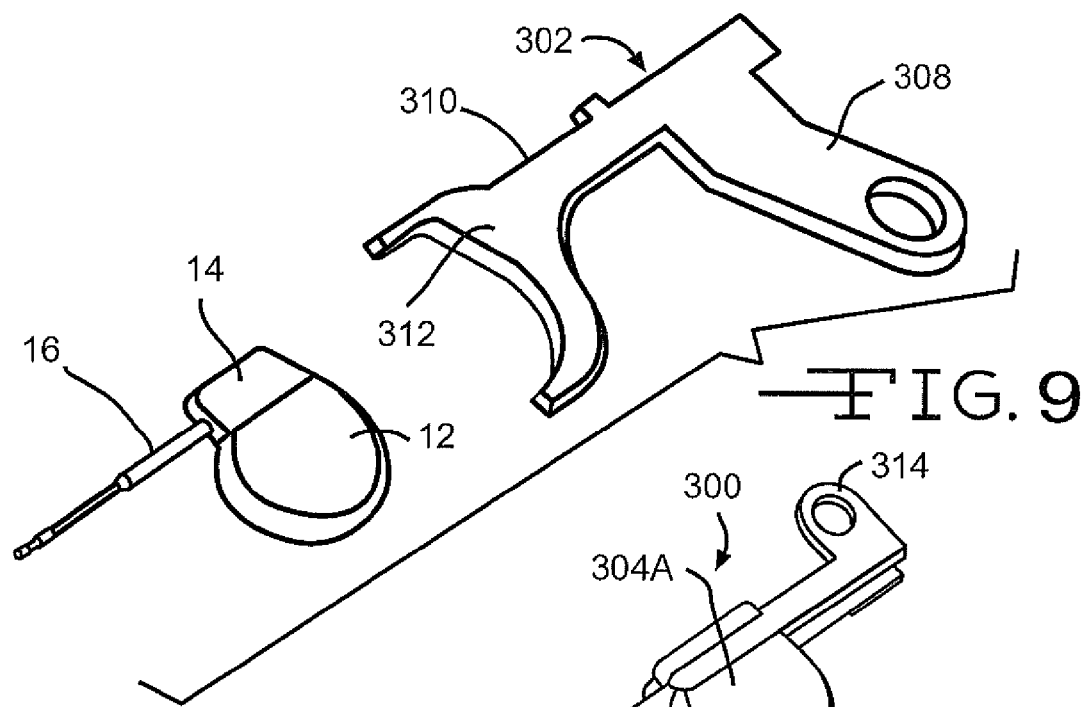
FIG. 9 is a perspective view of a third embodiment of a holder 302 separated from an implantable device 10 according to a third embodiment of the present invention.
Figure 10:
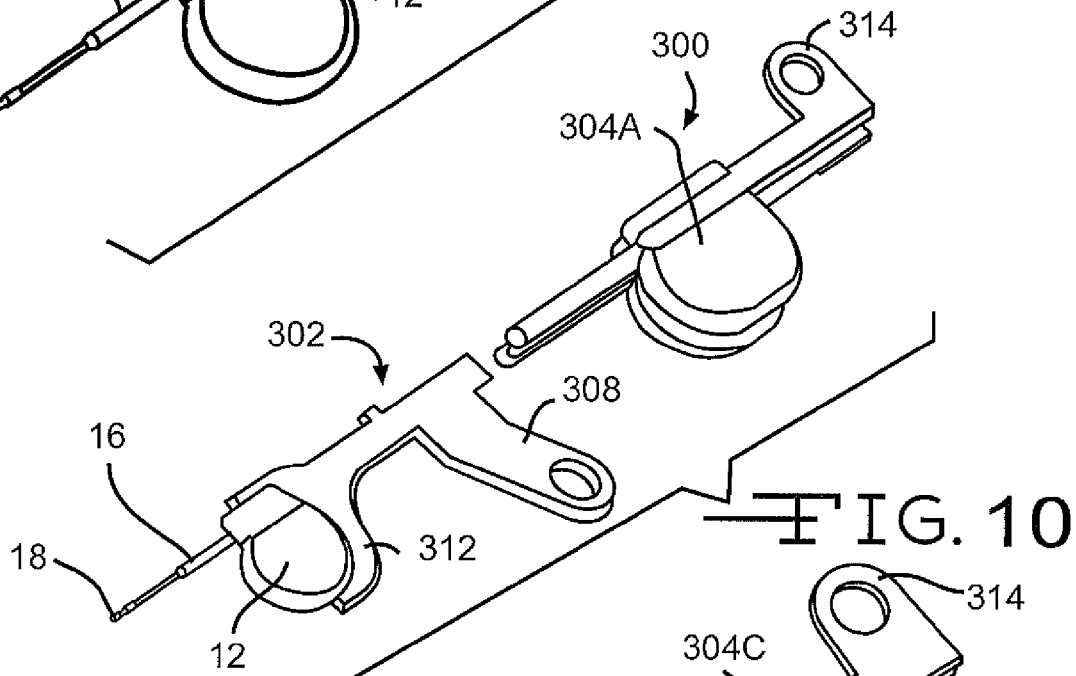
Figure 11:
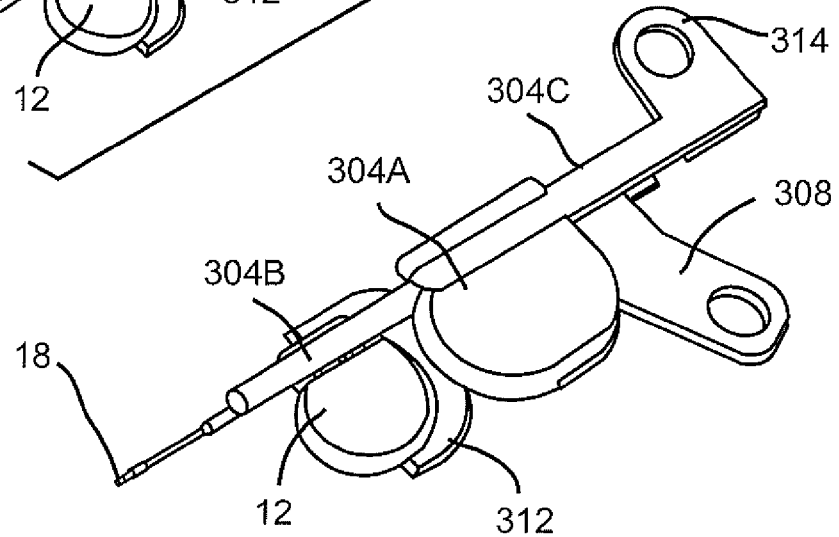
FIG. 11 is a perspective view showing the clamshells 304 and 306 just prior to being mated to each other with the holder 302 and implantable device 10 therebetween.
Figure 12:
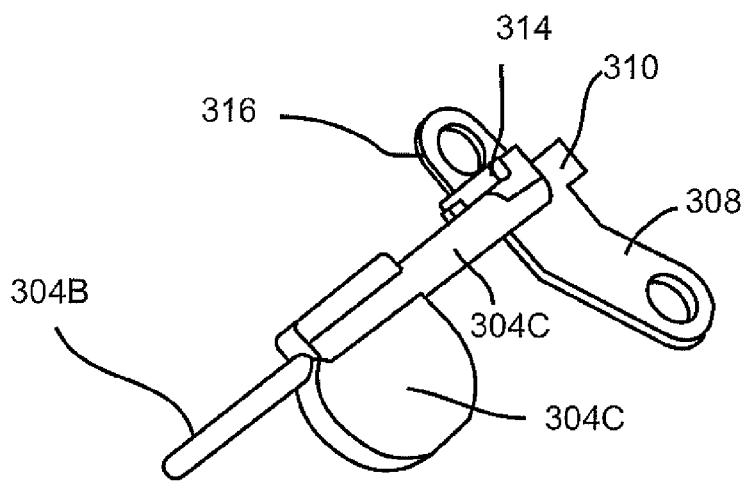
FIG. 12 is a perspective view showing the clamshells 304 and 306 mated to each other.

The antenna 16 of the ILR 10 is moved into and through the lumen of the sheath 208 with the housing 12 having been rotated (not shown) so that it is aligned with the U-shaped portion 204A of the lower leg 204 in a similar manner as previously described regarding the shaped body 228 of the dilator 220 being nested with the lower leg. The ILR 10 is next rotated so that it is nested with the tunneling tool as shown in FIG. 8. The ILR 10 is now located in the approximate position in which it is intended to be implanted. The upper and lower handles 212, 214 are then manipulated in opposite directions to each other. This movement causes the sheath 208 to break or separate along opposed lines of a surface modification 230 depicted by the dashed line in FIG. 9. Examples of such surface modifications include perforations, scoring of the sheath surface along the dashed line, notches or slits along the dashed line, or reduced material thickness along the dashed line such that the sheath 208 has reduced tensile strength there.

In this fashion, force applied to the sheath 208 as the tunneling tool 200 is withdrawn from the implant site location may cause the sheath to split along the surface modification 230, which will allow the tunneling tool to be pulled around the implantable device 10 and withdrawn from the body, leaving the implantable device 10 at the implant site location. Tissue trauma may be minimized during tunneling tool withdrawal because the sheath 208 may remain substantially flat against the implantable device 10 as the tunneling tool is withdrawn. In various implementations, a single type of surface modification or combinations of two or more surface modifications can be used. The resulting halves of the tunneling tool are then removed from the incision, leaving the ILR in place.

Figure 13:
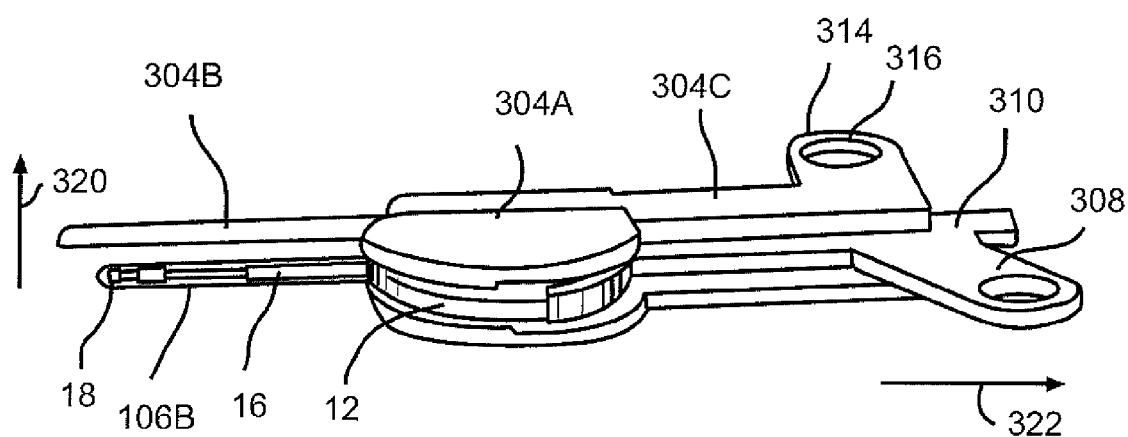
FIG. 13 is a perspective view showing the clamshells 304 and 306 being separated from each other during implantation of the device 10.
Figure 14:
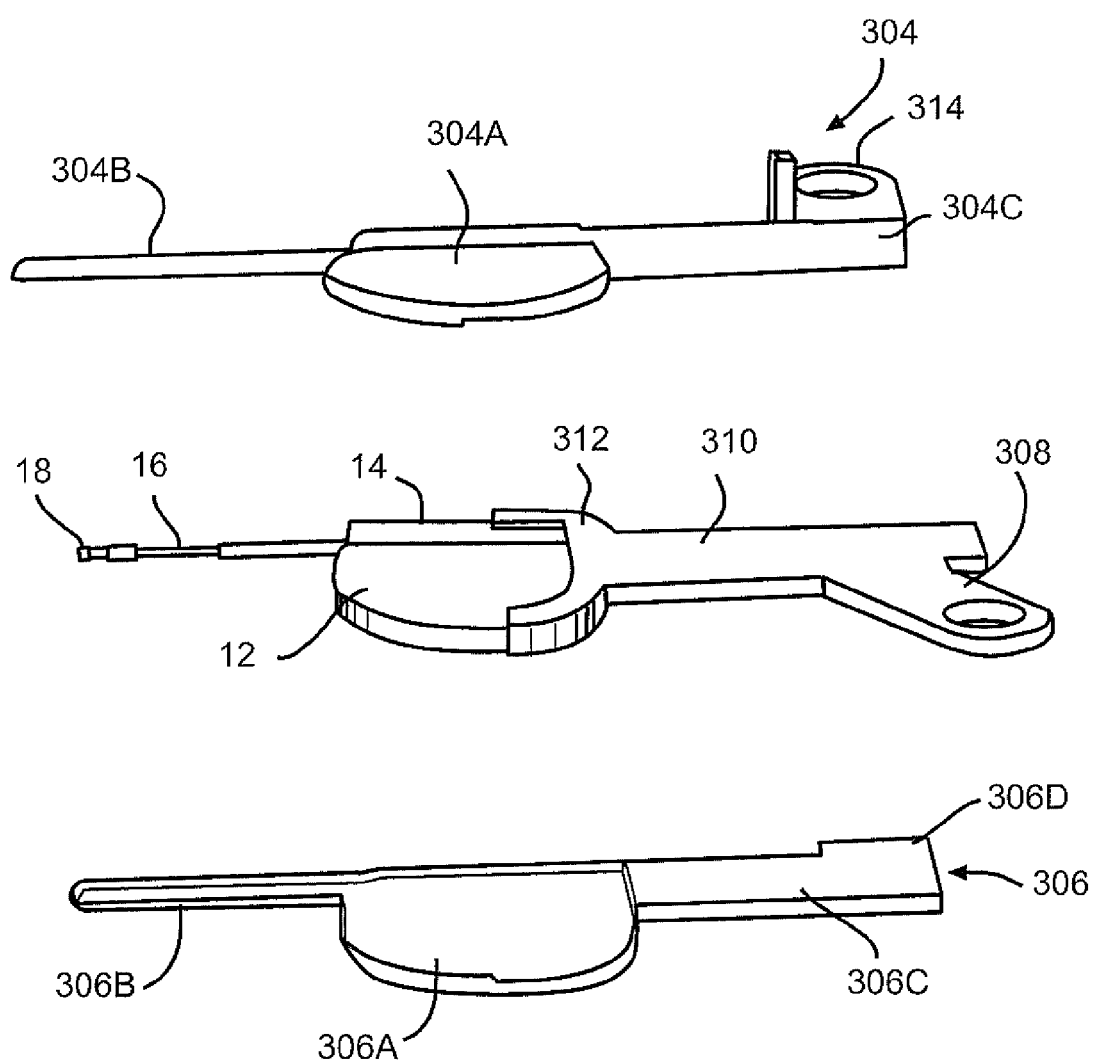
Figure 15:
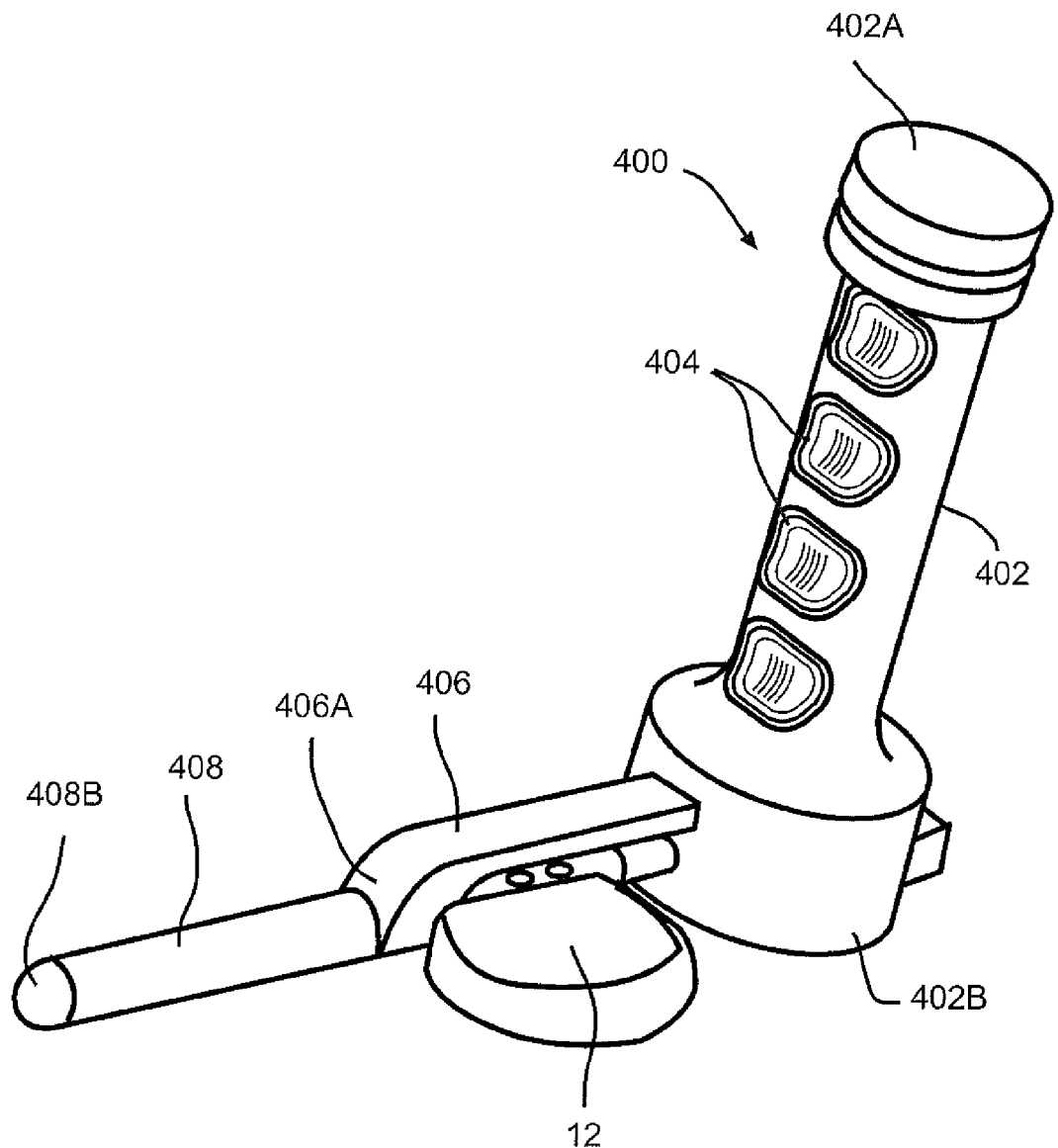
FIG. 15 is a perspective view of a fourth embodiment of a tunneling tool 400 according to the present invention holding an implantable device 10.
Figure 16A:
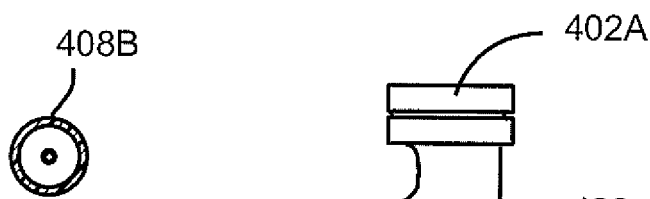
FIG. 16A is a cross-sectional view along line 16A-16A of FIG. 16.
Figure 16:
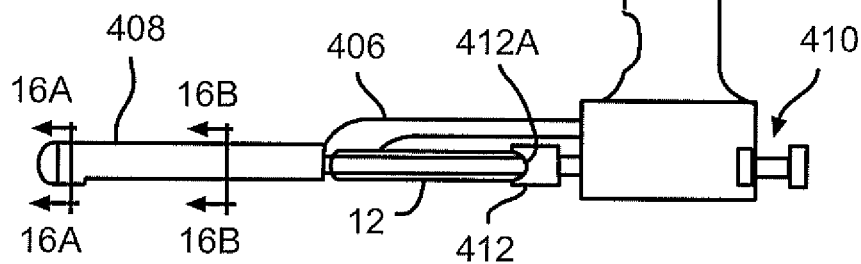
FIG. 16 is an elevational view of the tunneling tool 400 holding the implantable device 10.
Figure 16B:
FIG. 16B is a cross-sectional view along line 16B-16B of FIG. 16.
Figure 17:
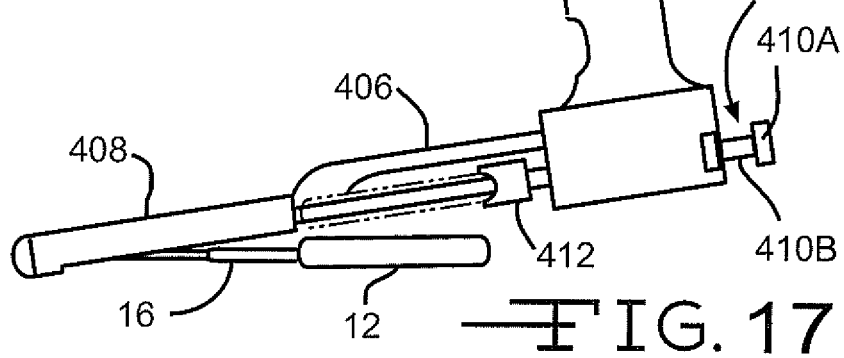
FIG. 17 is an elevational view, partly in phantom, showing the tunneling tool 400 just beginning to release from the implantable device 10.
Figure 18:
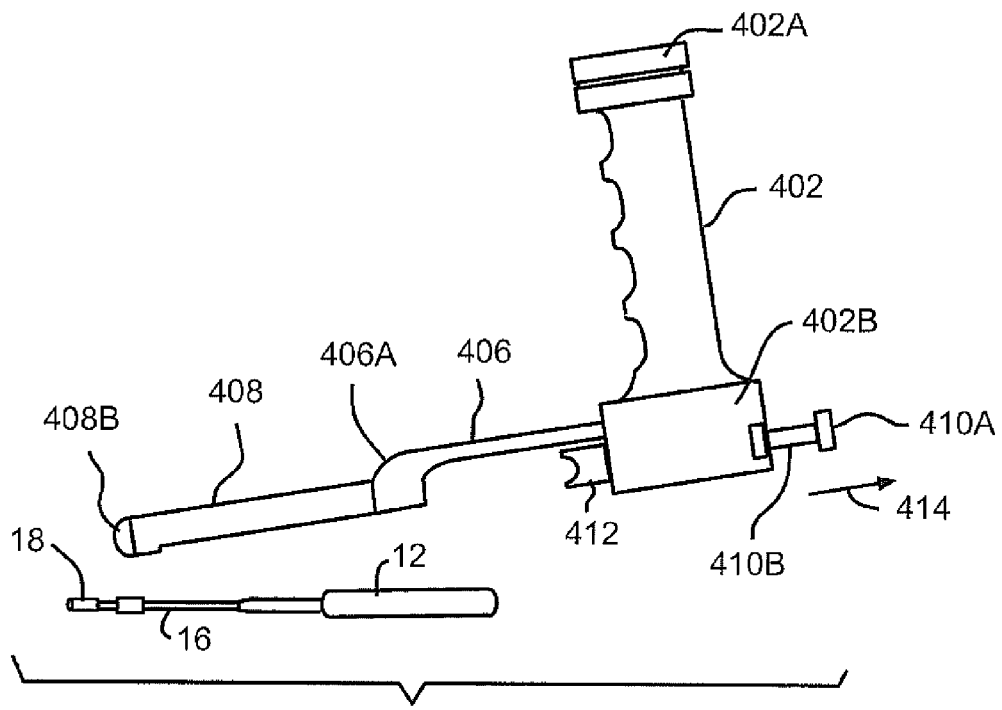
FIG. 18 is an elevational view showing the tunneling tool 400 of FIG. 17 fully separated from the implantable device 10.

FIGS. 9 to 14 illustrate a third embodiment of a tunneling tool 300 according to the present invention. The tunneling tool 300 comprises an ILR holder 302 that is housed inside upper and lower clamshell halves 304 and 306. The holder 302 is best illustrated in FIGS. 13 to 15 and comprises a handle grip 308 secured to the long edge of a web plate 310. A forwardly facing U-shaped distal nest 312 is secured to the end of web 310 opposite the handle grip 308. The holder 302 has a relatively thin thickness between opposed major sides of the handle grip 308, web plate 310 and U-shaped nest 312.

The clamshell portions 304 and 306 are similar to each other in some structure and different in other aspects. In that respect, the upper clamshell 304 comprises an upper housing portion 304A that is sized and shaped to cover one side of the ILR housing 12 and header 14 and the upper major side of the distal nest 312 of the holder 302. The upper clamshell 302 supports a distally extending channel-shaped member 304B. A proximally extending web plate 304C. A handgrip 314 having a finger opening 316 extends laterally upwardly from the proximal end of the proximal web plate 306C. A cross bar 316 is supported at the junction of the handgrip 314 and the web plate 304C. An upstanding protrusion 306D is supported at a proximal end of the web plate 304C.

Similarly, the lower clamshell 306 comprises a lower housing portion 306A that is sized and shaped to cover the opposite side of the ILR housing 12 and header 14 and the upper major side of the distal nest 312 of the holder 302. The lower clamshell 306 supports a distally extending channel-shaped member 306B. A proximally extending web plate 306C is supported by the lower clamshell housing portion 306A opposite the distal channel 306B.

In use, the ILR is moved into a nested relationship with the distal nest 312 with its antenna 16 extending outwardly opposite the holder 302. The holder/ILR subassembly is then received in the lower clamshell 306 with the antenna 16 laying in the lower distally extending channel 306B and the ILR received in the lower housing portion 306A. The upper clamshell 304 is then mated to the lower clamshell 306. This mated relationship serves to bring an edge of the respective upper and distal channels 304B, 306B, and upper and lower housings 304A, 306A together. The respective upper and lower web plates 304C, 306C lay against the opposite sides of the holder plate 310 with the ILR 10 housed inside the clamshells 304, 306. The resulting clamshells, holder and ILR assembly is then moved into an incision as described above with respect to tunneling tool 100 depicted in FIGS. 2A and 2B.

Once positioned at a desired location below the fascia, the one of the clamshells, for example the upper clamshell 304, is moved in a forwardly direction with respect to the lower clamshell 306. This relative movement causes the clamshells to partially separate from each other. The upper clamshell 304 is then moved in a lateral direction with respect to the lower clamshell 306, as indicated by arrow 20 in FIG. 14. Once separated, the ring 318 secured to the bottom clamshell is grasped and pulled in a rearwardly direction, as indicated by arrow 322. The cross-bar 314 secured to the upper clamshell 304 abuts the upstanding protrusion 306D of the upper clamshell 306 to thereby cause both clamshells 304, 306 to move together out of the incision, leaving the holder 302 and ILR behind. Finally, the holder 302 is grasped by the handle 308 and moved rearwardly and out of the incision, leaving the ILR implanted behind.

FIGS. 16, 16A, 16B and 17 to 19 illustrate a fourth embodiment of a tunneling tool 400 according to the present invention. The tunneling tool 400 comprises a generally cylindrically-shaped handgrip 402 having spaced apart and axially aligned finger depressions 404 extending along its length. An enlarged cylindrically portion 402A is at the proximal end of the handgrip. A distal cylindrically-shaped hub 402B resides at a distal end thereof. The distal hub 402B supports an extending leg 406 having an upwardly curving end 406A. An open sheath channel 408 having a generally inverted U-shaped cross-section extends outwardly from the curved end 406A of the leg 406. The sheath channel 408 has an elongated open channel 408A extending to a distal blunt end 408B.

The distal hub 402B further supports a spring-biased plunger 410. The plunger has a finger grip 410A at a proximal end of a shaft 410B. The shaft extends through the hub 402B aligned generally perpendicular to the handgrip 402 and parallel to the leg 406. A gripper block 412 comprising an inwardly curved face 412A is supported at the distal end of the shaft 410B.

Figure 19:
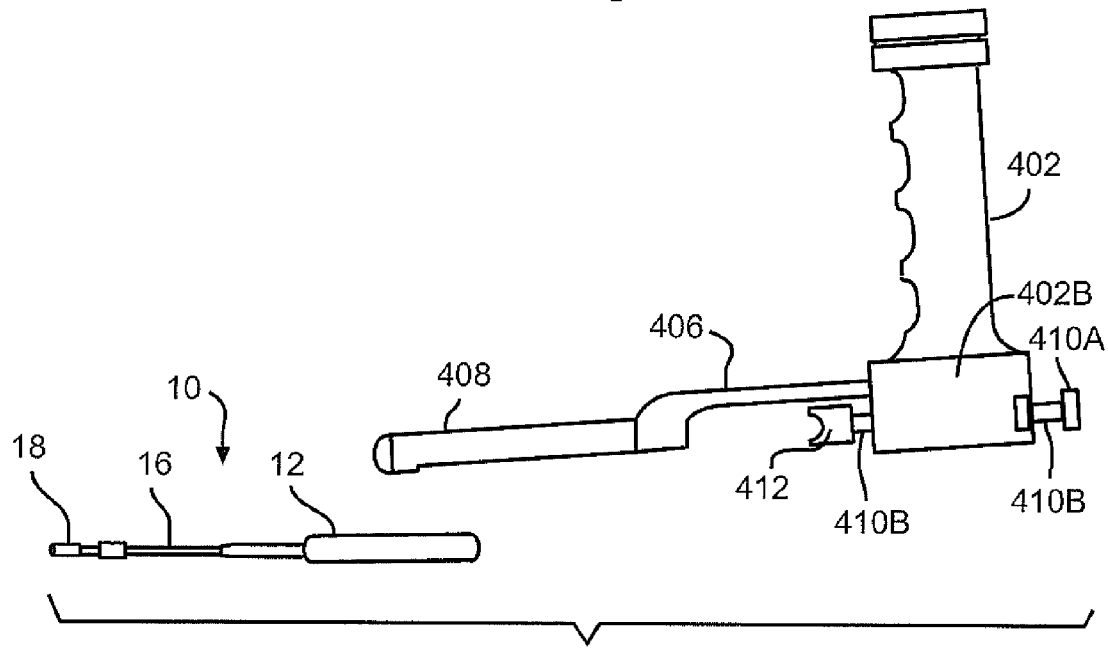
FIG. 19 is an elevational view showing the tunneling tool 400 of FIG. 18 being removed from body tissue, leaving the implantable device 10 behind.
Figure 20:
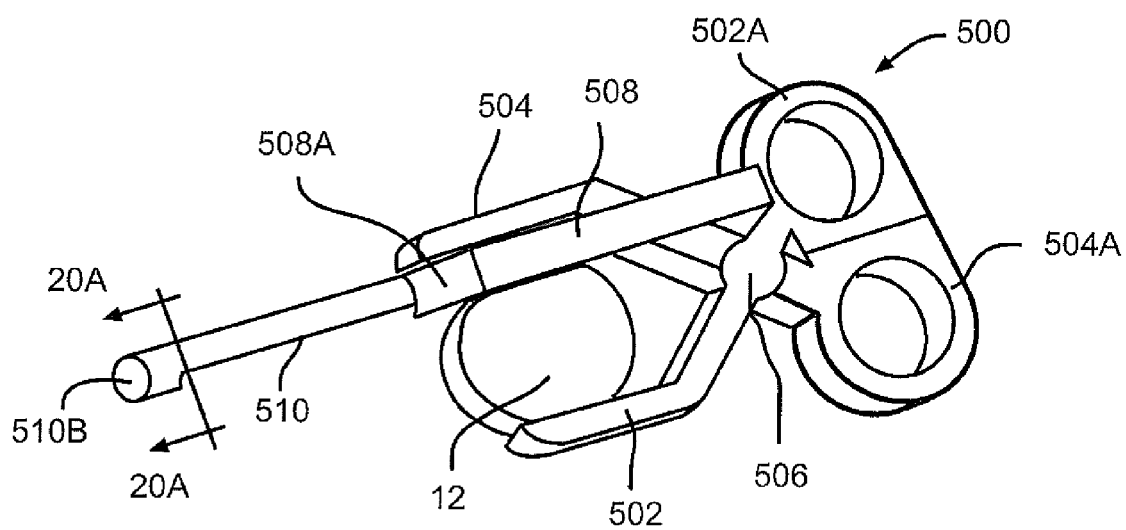
FIG. 20 is a perspective view showing a fifth embodiment of a scissors-type tunneling tool 500 according to the present invention in position to grasp an implantable device 10.
Figure 20A:
FIG. 20A is a cross-sectional view along line 20A-20A of FIG. 20.
Figure 21:
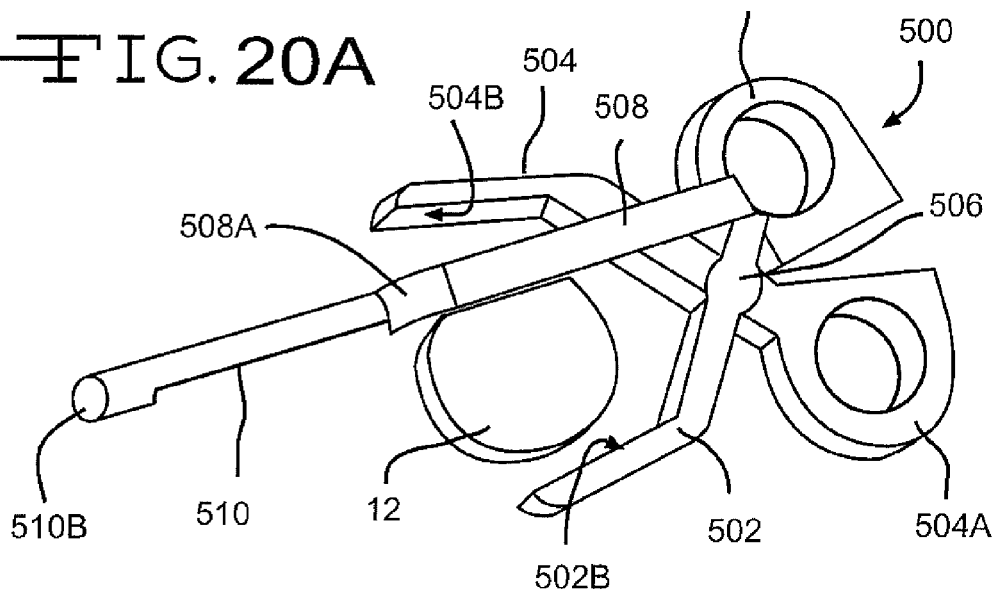
FIG. 21 is a perspective view showing the tunneling tool 500 grasping the implantable device 10.
Figure 22:
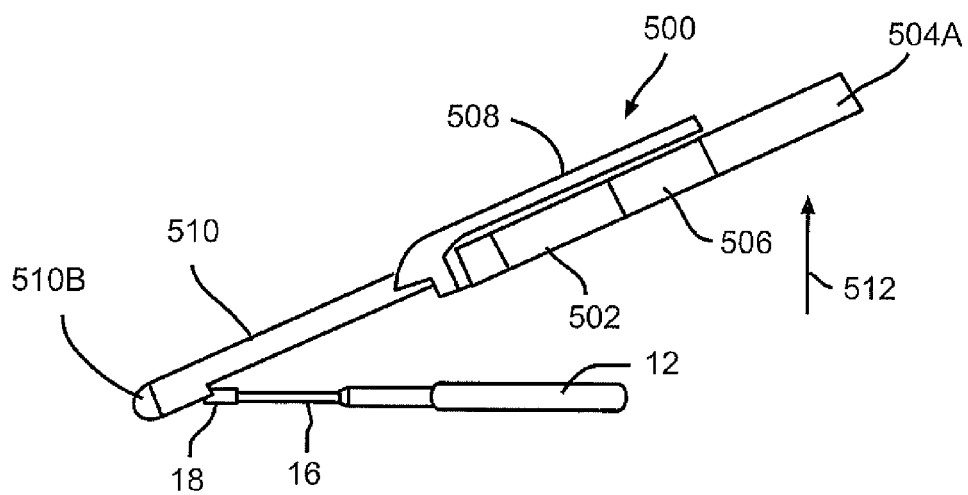
FIG. 22 is a side elevational view showing the tunneling tool 500 beginning to separate from the implantable device 10.

In use, the tunneling tool 400 is held by the grip 402 in one hand. The finger grip 410 is grasped by the other hand and pulled in a direction away from the leg 406 and sheath 408. The antenna 16 for the ILR 10 is then nested in the open channel 408A with the device housing 12 and header 14 aligned adjacent to the leg 406. The plunger 410 is released, which causes the gripper block 412 to contact the side edge of the ILR housing 12 and header 14 in a spring-biased fit. The ILR 10 is now firmly grasped or held by the tunneling tool 400. The blunt end 408B of the sheath 408 is then moved into an incision as described above with respect to tunneling tool 100 depicted in FIGS. 2A and 2B until the ILR 10 is at a desired location below the fascia. As shown in FIG. 19, the finger grip 410A for the plunger 410 is pulled in a direction opposite the ILR 10 (arrow 414) which causes the gripper block 412A to release from the edge of the ILR housing 12. The tunneling tool 400 is tilted and lifted in an upwardly direction away from the ILR including its housing 12, header 14 and antenna 16 to effect complete separation thereof. The tunneling tool 400 is then moved in a rearwardly direction out of the incision, leaving the ILR implanted in the body.

FIGS. 20, 20A and 21 to 23 illustrate a fifth embodiment of a tunneling tool 500 according to the present invention. The scissors-type tunneling tool 500 comprises opposed first and second legs 502 and 504 supporting respective finger rings 502A, 504A. The legs 502, 504 are pivotably connected to each other at an intermediate pivot 506. The first leg 502 extends from the pivot 506 to a distal, upwardly facing gripping face 502B. Similarly, the second leg 504 extends from the pivot 506 to a distal, downwardly facing gripping surface 504B that is aligned directly opposite the upwardly facing surface 502B. The first, upper finger ring 502 further supports an extending leg 508 having a curved portion 508A. A sheath 510 extends distally from the curved leg portion 508A. The sheath has an open elongated channel 510A that is aligned perpendicularly with the opposed faces 502B, 504B of the scissors legs 502, 504.

Figure 23:
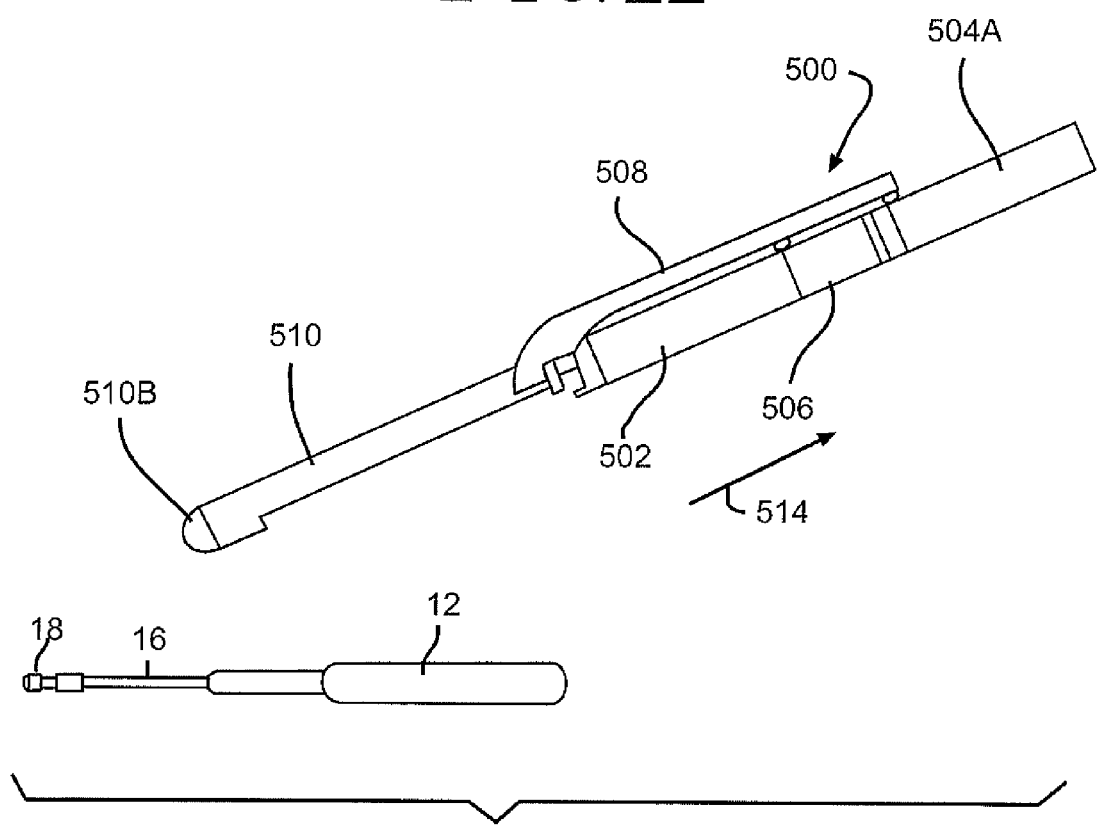
FIG. 23 is an elevational view showing the tunneling tool 500 being removed from body tissue, leaving the implantable device 10 behind.

In use, the finger rings 502A, 504A are manipulated in a scissors-like member to cause the respective legs 502, 504 to move apart from each other. The ILR antenna 16 is nested in the sheath channel 510A, centered between the scissor legs 502, 504. The scissor legs are closed to grasp the ILR in a firm manner. The blunt end 510B of the sheath 510 is then moved into an incision as described above with respect to tunneling tool 100 depicted in FIGS. 2A and 2B until the ILR 10 is at a desired location below the fascia. As shown in FIG. 23, the finger rings 502A, 502B are manipulated to open the scissors tunneling tool 500 and release the legs 502, 504 from the ILR 10. The tunneling tool 500 is moved in a lateral direction (arrow 512) away from the ILR to cause the sheath channel 510A to separate from the ILR including the antenna 16 (FIG. 23). The tunneling tool 500 is then moved in a rearwardly direction (arrow 514) out of the incision, leaving the ILR implanted in the body.

In various implementations, any one of the tunneling tools 100, 200, 300, 400 and 500 may be formed of a high density polyethylene (HDPE), or of poly-tetrafluoroethene (PTFE). In some implementations, the tunneling tools may be radiopaque.

FIG. 25 is a diagram of an exemplary system 700 including an implantable device 10 implanted in a body of a patient 702. The implantable device 10 may correspond to any of the implantable devices discussed herein and may be implanted according to any of the introduction techniques disclosed herein. When implanted, the device 10 may collect biological data from the patient 702. A handheld computing device 704 may be programmed to communicate wirelessly (e.g., transmit or receive data via radio frequency telemetry) with the implantable device 10. In some implementations, an external charging device 706 may be used to periodically recharge a battery of the implantable device 10, though as discussed above the device 10 may alternatively use a single-use battery in some implementations. In various implementations, the patient 702 may use the handheld device 704 to manually initiate data collection by the implanted device 10 (e.g., initiate ECG signal sensing and recording). For example, if the patient 702 feels lightheaded or feels palpitations in her chest, she may press a button 708 on the handheld device 704, and the handheld device may wirelessly command the implanted device 10 to record and store physiologic data. The implanted device 10 may also record a physiologic signal when it determines that such recordation may provide useful information. For example, the device may monitor a biological parameter (e.g., heart rate), and may record an ECG signal based on predetermined characteristics of the biological parameter. In some implementations, the device 10 may periodically record sensed physiologic information according to a predetermined schedule. For example, the device may record a strip of data (e.g., covering a predetermined number of heart beats or having a predetermined strip duration or length) once every minute, every several minutes, every hour, every several hours, every day, every several days, etc.

The implanted device 10 may periodically transmit collected data to the handheld device 704, such as every few hours or once per day, for example. In some implementations, the implantable device 10 may transmit sensed data in real time to the handheld device 704, and the handheld device may store the data in internal memory or display the data as a waveform or otherwise on a display screen 710 of the handheld device 704. In some implementations, functionality of the handheld device 704 and the charger 706 may be combined within a single device.

A base station 712 may communicate (e.g., wirelessly) with the handheld device 704 and/or the charger 706, and may receive data from (or send data to) either device in various implementations. The base station 712 may transmit data over a network 714 to a remote server device 716, where the data may be processed and analyzed (e.g., by a physician or a health care provider). In some implementations, data analysis may occur within the implanted device 10, the handheld device 704, the charger 706, or the base station 712. Data analysis can include detection of cardiac anomalies based on the collected data.

Exemplary widths of the implantable device 10 discussed herein may be, at its widest point, about 17.8 mm in one implementation and about 22.1 mm in an alternative implementation, though even smaller widths are possible. With devices having these widths, skin incisions as narrow as 13.5 mm or 17 mm may be possible.

A layer of tissue, referred to as fascia, covers the pectoral muscle. In some implementations, the implantable device 10 may be introduced to a sub-fascial implant location. In some cases, introducing the device 10 to a sub-fascial location may reduce a risk of erosion and may provide a more stable implant location. In some implementations, the device 10 may be implanted such that the entire device remains above the pectoral fascia. In alternative implementations, the fascia may be penetrated and the device 10 may be implanted such that the entire device is located below the pectoral fascia. In yet other implementations, the fascia may be penetrated and the device 10 may be implanted such that a distal portion of the device is positioned below the fascia and a proximal portion of the device is positioned above the fascia.

It is appreciated that various modifications to the inventive concepts described herein may be apparent to those skilled in the art without departing from the spirit and scope of the present invention defined by the hereinafter appended claims.

What is claimed is:

1. A tunneling tool for implanting an implantable medical device (IMD) in a body tissue, the tunneling tool comprising:
   a) a shaft extending along a longitudinal axis from a proximal handle to a distal piercing tip, the shaft comprising:
      i) a tab extending from the shaft and being spaced proximally from the piercing tip and distally from the handle, wherein the tab has a first slot spaced from the longitudinal axis; and
      ii) a second slot in the handle, wherein the second slot is spaced laterally from the longitudinal axis of the shaft,
      iii) wherein the shaft comprises an inverted U-shaped channel portion that is sized and shaped for an antenna of the IMD to nest therein; and
   b) a rip cord extending from a distal rip cord end releasably secured to the shaft to a proximal rip cord end disposed adjacent to the handle, wherein the rip cord is in a movable relationship received in the first and second slots,
   c) wherein with the IMD contacting the shaft, the distal rip cord end is releasably secured to the shaft at a position distal to the IMD with the rip cord extending around and contacting a portion of the IMD, opposite the shaft, and then passing through the first and second slots to thereby releasably secure the IMD to the shaft, and
   d) wherein with the IMD secured to the shaft, the tunneling tool is movable into a body tissue and to a desired implant location, and then the proximal rip cord end is manipulatable in a proximal direction to release the distal rip cord end from the shaft so that the rip cord slides along the first and second slots and out of contact with the IMD, and
   e) wherein the tunneling tool is then manipulatably removable from the tissue, thereby leaving the IMD implanted therein.

2. The tunneling tool of claim 1 wherein the handle comprises a plate and the second slot extends through the plate.

3. The tunneling tool of claim 1 wherein the first and second slots are of generally rectangular cross-sections with their respective longitudinal axis aligned generally parallel to the longitudinal axis of the shaft.

4. The tunneling tool of claim 1 wherein the shaft comprises a planar wall section, and wherein a first imaginary plane of the planar wall is aligned generally perpendicular to a second imaginary plane aligned along the tab extending from the shaft.

5. The tunneling tool of claim 1 wherein the shaft comprises a planar wall section, and wherein a first imaginary plane of the planar wall is aligned generally perpendicular to a second imaginary plane aligned along the tab extending from the shaft, and wherein the planar wall section of the shaft is intermediate to the inverted U-shaped channel portion of the shaft and the tab.

6. The tunneling tool of claim 1 wherein the shaft has a circular cross-section extending from the handle to the tab.

7. The tunneling tool of claim 1 wherein the shaft comprises a polyethylene material.

8. The tunneling tool of claim 1 wherein the inverted U-shaped channel portion of the shaft is sufficiently flexible to deflect upon the tip contacting a muscle tissue.

9. The tunneling tool of claim 1 wherein the first slot is aligned axially with the second slot.

10. The tunneling tool of claim 1 wherein with the IMD contacting the shaft, the first and the second slots are proximal to the IMD.

11. A tunneling tool for implanting an implantable medical device (IMD) in a body tissue, the tunneling tool comprising:
   a) a shaft extending along a longitudinal axis from a proximal handle to a distal piercing tip, the shaft comprising:
      i) an inverted U-shaped channel portion that is sized and shaped for an antenna of the IMD to nest therein;
      ii) a tab extending from the shaft and being spaced distally from the handle, wherein the tab has a first slot spaced from the longitudinal axis and the inverted U-shaped channel is disposed between the distal piercing tip and the tab; and iii) a second slot in the handle, wherein the second slot is spaced laterally from the longitudinal axis of the shaft and the second slot is aligned axially with the first slot; and
b) a rip cord extending from a distal rip cord end releasably secured to the shaft to a proximal rip cord end disposed adjacent to the handle, wherein the rip cord is in a movable relationship received in the first and second slots,
c) wherein with the IMD contacting the shaft, the antenna of the IMD nests in the inverted U-shaped channel with the distal rip cord end releasably secured to the shaft at a position distal to the IMD and with the rip cord extending over the antenna and around and contacting a portion of the IMD, opposite the shaft, and then passing through the first and second slots to thereby releasably secure the IMD to the shaft, and
d) wherein with the IMD secured to the shaft, the tunneling tool is movable into a body tissue and to a desired implant location, and then the proximal rip cord end is manipulatable in a proximal direction to release the distal rip cord end from the shaft so that the rip cord slides along the first and second slots and out of contact with the IMD, and
e) wherein the tunneling tool is then manipulatably removable from the tissue, thereby leaving the IMD implanted therein.

12. The tunneling tool of claim 11 wherein the shaft comprises a planar wall section extending from the tab to the inverted U-shaped channel portion, the inverted U-shaped channel portion extending distally to the piercing tip, and wherein the inverted U-shaped channel is sized and shaped to nest the antenna of the IMD with the IMD contacting the planar wall section of the shaft.

13. The tunneling tool of claim 12 wherein a first imaginary plane of the planar wall section is aligned generally perpendicular to a second imaginary plane aligned along the tab extending from the shaft.

14. The tunneling tool of claim 11 wherein with the IMD contacting the shaft, the first and the second slots are proximal to the IMD.

15. A tunneling tool for implanting an implantable medical device (IMD) in a body tissue, the tunneling tool comprising:
a) a shaft extending along a longitudinal axis from a proximal handle to a distal piercing tip, the shaft comprising:
i) a tab extending from the shaft and being spaced proximally from the piercing tip and distally from the handle, wherein the tab has a first slot spaced from the longitudinal axis; and
ii) a second slot in the handle, wherein the second slot is spaced laterally from the longitudinal axis of the shaft,
iii) wherein the first and second slots are of generally rectangular cross-sections with their respective longitudinal axis aligned generally parallel to the longitudinal axis of the shaft; and
b) a rip cord extending from a distal rip cord end releasably secured to the shaft to a proximal rip cord end disposed adjacent to the handle, wherein the rip cord is in a movable relationship received in the first and second slots,
c) wherein with the IMD contacting the shaft, the distal rip cord end is releasably secured to the shaft at a position distal to the IMD with the rip cord extending around and contacting a portion of the IMD, opposite the shaft, and then passing through the first and second slots to thereby releasably secure the IMD to the shaft, and
d) wherein with the IMD secured to the shaft, the tunneling tool is movable into a body tissue and to a desired implant location, and then the proximal rip cord end is manipulatable in a proximal direction to release the distal rip cord end from the shaft so that the rip cord slides along the first and second slots and out of contact with the IMD, and
e) wherein the tunneling tool is then manipulatably removable from the tissue, thereby leaving the IMD implanted therein.

16. The tunneling tool of claim 15 wherein the handle comprises a plate and the second slot extends through the plate.

17. The tunneling tool of claim 15 wherein the shaft comprises a planar wall section, and wherein a first imaginary plane of the planar wall is aligned generally perpendicular to a second imaginary plane aligned along the tab extending from the shaft.

18. The tunneling tool of claim 15 wherein the shaft comprises an inverted U-shaped channel portion that is sized and shaped for an antenna of the IMD to nest therein.

19. The tunneling tool of claim 18 wherein the inverted U-shaped channel portion of the shaft is sufficiently flexible to deflect upon the tip contacting a muscle tissue.

20. The tunneling tool of claim 18 wherein the shaft comprises a planar wall section, and wherein a first imaginary plane of the planar wall is aligned generally perpendicular to a second imaginary plane aligned along the tab extending from the shaft, and wherein the planar wall section of the shaft is intermediate to the inverted U-shaped channel portion of the shaft and the tab.

* * * * *